(12) United States Patent
Rodriguez et al.

(10) Patent No.: US 6,877,877 B2
(45) Date of Patent: Apr. 12, 2005

(54) SINGLE INTRAVENOUS DRIP COMPONENT ILLUMINATION DEVICE

(75) Inventors: Joel J. Rodriguez, Gloucester, MA (US); Richard A Simmers, Gloucester, MA (US); Joan O'Donnell, Wilmington, MA (US); Alejandro Berenstein, New York, NY (US)

(73) Assignee: Embo-Optics, LLC, Gloucester, MA (US)

( * ) Notice: Subject to any disclaimer, the term of this patent is extended or adjusted under 35 U.S.C. 154(b) by 90 days.

(21) Appl. No.: 10/366,021

(22) Filed: Feb. 13, 2003

(65) Prior Publication Data

US 2004/0160770 A1 Aug. 19, 2004

(51) Int. Cl.$^7$ ................................................ F21V 9/00
(52) U.S. Cl. ..................... 362/231; 362/572; 362/804; 362/800; 362/431; 604/253
(58) Field of Search ................................ 362/551, 572, 362/804, 431, 231, 800; 604/253

(56) References Cited

U.S. PATENT DOCUMENTS

| | | |
|---|---|---|
| 3,217,709 A | 11/1965 | Schneider et al. |
| 3,563,090 A | 2/1971 | Deltour |
| 3,590,809 A | 7/1971 | London |
| 3,641,543 A | 2/1972 | Rigby |
| 3,690,318 A | 9/1972 | Gorsuch |
| 4,453,204 A | 6/1984 | Warshawsky |
| 4,498,901 A | 2/1985 | Finch |
| 4,673,397 A | 6/1987 | Lynn et al. |
| 4,976,687 A | 12/1990 | Martin |
| 5,045,069 A | 9/1991 | Imparato |
| 5,346,466 A | 9/1994 | Yerlikaya et al. |
| 5,351,168 A | 9/1994 | Easley |
| 5,425,730 A | 6/1995 | Luloh |
| 5,690,612 A | 11/1997 | Lopez et al. |
| 5,843,045 A | 12/1998 | DuPont |
| 6,050,713 A * | 4/2000 | O'Donnell et al. ......... 362/551 |
| 6,604,847 B2 * | 8/2003 | Lehrer ........................ 362/572 |

* cited by examiner

Primary Examiner—Stephen Husar
Assistant Examiner—James W Cranson, Jr.
(74) Attorney, Agent, or Firm—Epstein Becker & Green, PC; John M. Garvey; Michel Morency

(57) ABSTRACT

A single intravenous drip components illumination device containing a source of light that can illuminate IV bags or bottles, drip chambers and tubing. The directed light of the light source provides adequate lighting for use of the invention in unlit or dimly lit settings with minimum lateral scattering. The invention is powered by an external AC or DC power supply and/or by batteries mounted internally to the base of the invention.

9 Claims, 3 Drawing Sheets

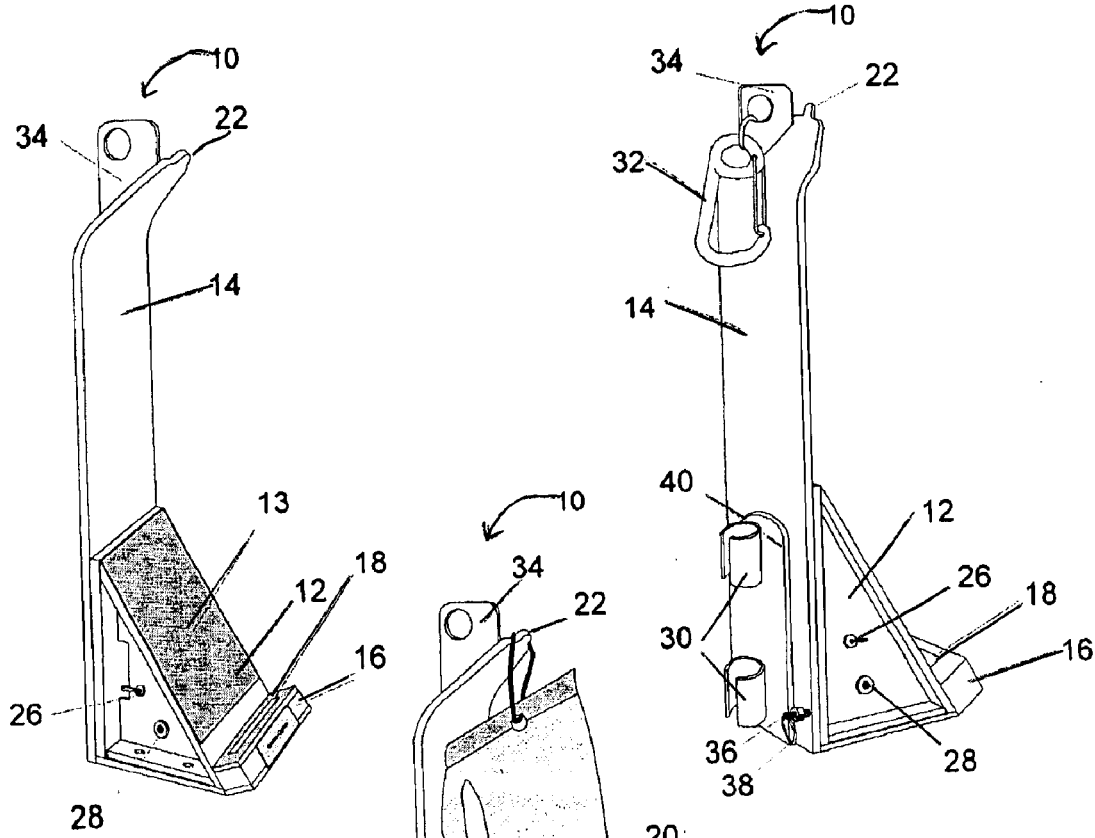
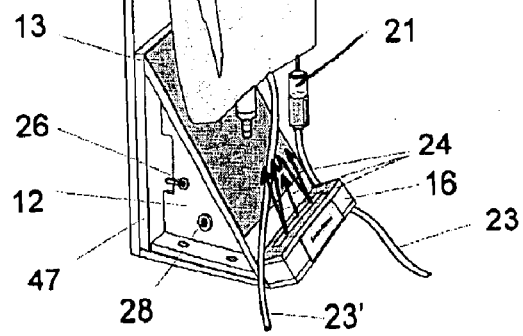

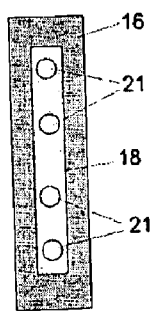
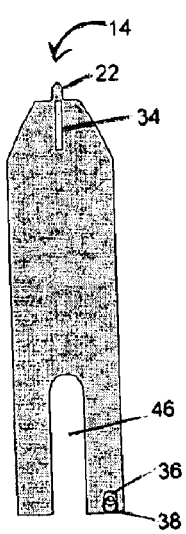
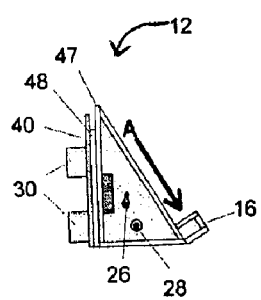
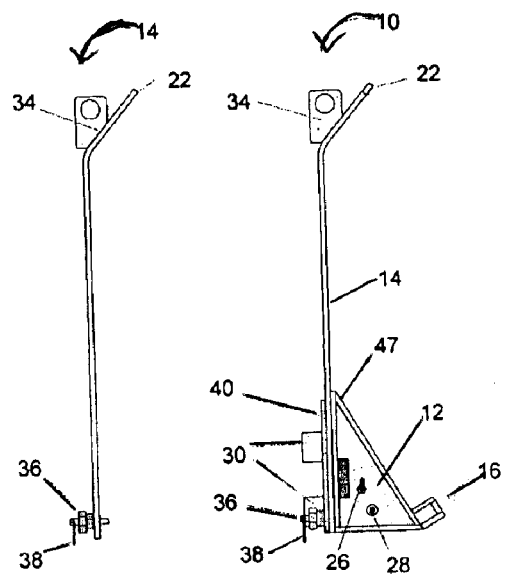
FIGURE 2B
FIGURE 2A  FIGURE 2C  FIGURE 2D  FIGURE 2E

SINGLE INTRAVENEOUS DRIP COMPONENT ILLUMINATION DEVICE

BACKGROUND OF INVENTION

1. Field of Invention

The present invention relates to an illumination method and device for use during interventional or diagnostic procedures. It further relates to the illumination of intravenous (IV) drip components such as IV medication/solution bags, their drip chambers and tubing during interventional or diagnostic procedures.

2. Background of the Invention

IV fluids are generally supplied to a patient under the force of gravity by positioning an IV bag containing the IV fluid at an elevated position relative to the patient. The rate of flow is set by a manually adjustable clamp positioned in the line between the IV bag and the patient. The fluid flows to the patient via a drip chamber attached to the lower, or outlet end of the IV bag. The drip chamber generates discrete, successive drops that fall from the drip chamber into a reservoir defined at the lower end of the drip chamber from which the fluid flows to the patient via an IV delivery tube.

The IV bag is transparent so that its fluid level may be observed by medical personnel. The drip chamber is also transparent so that the drips may be observed by an anesthesiologist or other medical personnel to ensure that the drippage is occurring and to further ensure that the drippage rate is within the appropriate predetermined limits.

It is especially critical that a proper drippage rate be maintained and verified during surgical or diagnostic procedures. However, an increasing number surgical procedures are being performed using fluoroscopy, in a dark room or a room with only ambient lighting since any direct light will compromise the performance of the radiologist or any medical professional, or integrity of the procedure, with resulting risk to the patient. The medical team must be able to clearly view the IV drip chamber and confirm a constant fluid drip is being maintained in order to prevent a life-threatening clot from forming at the tip of a catheter which is utilized throughout the interventional procedure.

It is also critical that a proper drippage rate be maintained and verified for patients who require medical infusions of medication around the clock. Often, a patient requires medication every two or four hours. In order to properly administer medication to patients on a 24-hour basis, including during the hours of darkness or in patient rooms that are dark, the healthcare worker must either turn the lights on in the patient's room or use a portable flashlight.

The constant disturbing of the patient every two or four hours to administer medication, check the IV drip rate or to check the amount of solution in the IV bag results in the patient being unable to obtain a necessary period of restful sleep. This lack of uninterrupted sleep results in a recognized psychological disorder referred to as Intensive Care Unit Psychosis. Importantly, the ability of patients to recover from their ailments is endangered because of the deprivation of proper rest.

It is therefore an object of the invention to provide a compact and portable device that is able to support IV drip components such as an IV bag, its drip chamber and tubing and provide a localized light source that is accurately directed thereat so that a healthcare professional in an unlit, dimly or normally lit room can easily and accurately determine that drippage is in fact occurring and/or is occurring at the predetermined satisfactory rate. It is especially critical that proper drippage rate be maintained and verified during any medical, surgical or diagnostic procedure.

SUMMARY OF THE INVENTION

In accordance with the present invention, there is provided a compact and portable device that is able to support IV drip components such as an IV medication/solution bag, its drip chamber and tubing. The device also provides a localized light source that is accurately directed at the IV drip components so that a determination that drippage is in fact occurring and/or is occurring at the predetermined satisfactory rate may be easily and accurately made, even in an unlit, dimly lit or normal ambient lit environment.

In its most general form, the device consists of a light containing base portion and an adjustable and removable back portion. The base portion contains a light source that can be powered by internally stored batteries, rechargeable or not, or an external low-voltage power supply or by a combination of batteries and external power source. In one embodiment of the invention, light emitting diodes (LEDs) are used as the light source. Other light sources while being in association the other aspects of the present invention form several embodiments. Examples of such other light sources include, but are not limited to fiber optic lights, phosphorescent lights, fluorescent lights or tungsten containing devices (e.g., light bulbs), etc.

The back portion is designed for supporting IV drip components such as an IV medication/solution bag, its drip chamber and tubing. The back portion may be adjustable in order to accommodate IV drip components of different sizes or to accommodate other situations wherein the greater overall height of the IV drip components might be useful.

The invention can be used in a wide variety of ambulatory field environments. In one embodiment, the invention may be used as a stand-alone device. That is, it may be attached to a tabletop or any surface or plane by way of a retention means. In another embodiment, the invention may be hung from virtually any conceivable support structure. In yet another embodiment, the invention may be attached to a vertical IV support pole by means of brackets on the back portion.

BRIEF DESCRIPTION OF THE DRAWINGS

A complete understanding of the present invention may be obtained by reference to the accompanying drawings, considered in conjunction with the subsequent detailed description.

FIG. 1A is a perspective view of the front and side portions of the single intravenous drip component illumination device according to the present invention;

FIG. 1B is a perspective view of the side and rear of the single intravenous drip components illumination device;

FIG. 1C is a perspective view of the front and side of the single intravenous drip components illumination device with an intravenous drip bag and drip chamber suspended therefrom;

FIG. 2A is an orthogonal side view of the light-containing base portion of the single intravenous drip component illumination device according to the present invention;

FIG. 2B is an orthogonal top view of the base illuminator assembly;

FIG. 2C is an orthogonal rear view of the moveable back portion of the single intravenous drip component illumination device;

FIG. 2D is an orthogonal side view of the moveable back portion of the single intravenous drip component illumination device;

FIG. 2E is an orthogonal side view of the assembled base portion and moveable back portion of the single intravenous drip components illumination device according to the present invention;

IDENTIFICATION OF ITEMS IN THE FIGURES

Figure 3A:
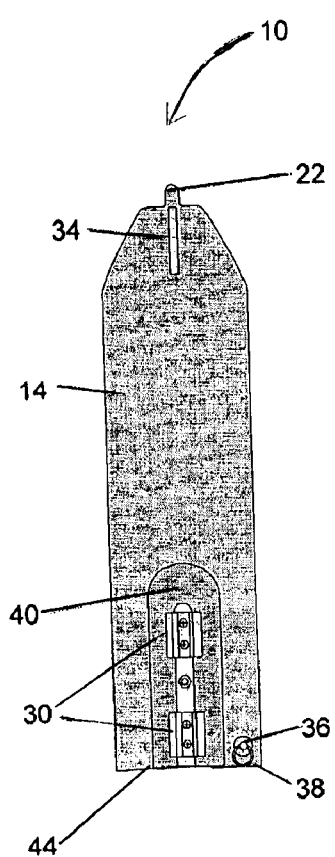
FIG. 3A is an orthogonal rear view of the moveable back portion shown in its lower position relative to the light-containing base portion.

For purposes of clarity and brevity, like elements and components will bear the same designations and numbering throughout the FIGURES.

FIG. 1A
- 10—the single intravenous drip components illumination device invention
- 12—base portion
- 13—darkened external surface of base portion
- 14—moveable back portion
- 16—base illuminator assembly
- 18—window (for light)
- 22—nib for supporting IV bag
- 26—on/off switch
- 28—electric power receptacle
- 34—integral structure with hole therethrough FIG. 1B
- 10—the single intravenous drip components illumination device invention
- 12—base portion
- 14—moveable back portion
- 16—base illuminator assembly
- 18—window (for light)
- 22—nib for supporting IV bag
- 26—on/off switch
- 28—electric power receptacle
- 30—brackets for engaging standard IV pole
- 32—hook
- 34—integral structure with hole therethrough
- 36—spring-loaded release
- 38—finger pull ring on spring release 36
- 40—flange for supporting moveable back portion FIG. 1C
- 10—the illuminated IV drip device invention
- 12—base portion
- 13—darkened external surface of base portion
- 16—base illuminator assembly
- 20—IV drip bag
- 21—drip chamber
- 22—nib for supporting IV bag
- 23, 23'—IV line
- 24—light rays
- 26—on/off switch
- 28—electric power receptacle
- 34—integral structure with hole therethrough
- 47—back side of base portion FIG. 2A
- 12—base portion
- 16—base illuminator assembly
- 26—on/off switch
- 28—electric power receptacle
- 30—brackets for engaging standard IV pole

- 40—flange for supporting moveable back portion
- 47—back side of base portion
- 48—sheet of material disposed between the flange 40 and the back wall 47 of the base portion 12

FIG. 2B
- 16—base illuminator assembly
- 18—window
- 21—LEDs

FIG. 2C
- 14—moveable back portion
- 22—nib for supporting IV bag
- 34—integral structure with hole therethrough
- 36—spring-loaded release
- 38—finger pull ring on spring release 36
- 46—slot for engaging item 48 on back side of base portion FIG. 2D
- 14—moveable back portion
- 22—nib for supporting IV bag
- 34—integral structure with hole therethrough
- 36—spring-loaded release
- 38—finger pull ring on spring release 36

FIG. 2E
- 10—the single intravenous drip components illumination device invention
- 12—base portion
- 14—moveable back portion
- 16—base illuminator assembly
- 22—nib for supporting IV bag
- 26—on/off switch
- 28—electric power receptacle
- 30—brackets for engaging standard IV pole
- 34—integral structure with hole therethrough
- 36—spring-loaded release
- 38—finger pull ring on spring release 36
- 40—flange for supporting moveable back portion
- 47—back side of base portion FIG. 3A
- 10—the single intravenous drip components illumination device invention
- 14—moveable back portion
- 22—nib for supporting IV bag
- 30—brackets for engaging standard IV pole
- 34—integral structure with hole therethrough
- 36—spring-loaded release
- 38—finger pull ring on spring release 36
- 40—flange for supporting moveable back portion
- 44—bottom side of base portion FIG. 3B
- 10—the single intravenous drip components illumination device invention
- 12—base portion
- 14—moveable back portion
- 22—nib for supporting IV bag
- 30—brackets for engaging standard IV pole
- 34—integral structure with hole therethrough
- 36—spring-loaded release
- 38—finger pull ring on spring release 36
- 40—flange for supporting moveable back portion
- 42—hole in back side of base portion
- 44—bottom side of base portion
- 46—slot for engaging item 48 on back side of base portion
- 47—back side of base portion

DETAILED DESCRIPTION OF THE PREFERRED EMBODIMENTS

The present invention is an intravenous illuminator apparatus designed for illuminating an intravenous (IV) drip chamber, IV tubing and medication/solutions bag(s). The apparatus consists of a universal, adjustable, holder bracket for use with a solution/medication bag and IV drip chamber and tubing, and it incorporates a base illuminator assembly or light source that is battery powered (DC) and/or AC powered via the use of a universal power supply/charger.

The IV illuminator apparatus according to the present invention also employs attachment brackets that facilitate the use of this device with any standard IV pole. More generally, the apparatus is comprised of a base portion and a detachable back portion. The detachable back portion is designed to hold or support any typical IV solution bag or bottle along with an IV drip chamber and tubing. The inventors envision that the present apparatus may be ganged, or attached together, for use when multiple IV solutions or medications are being dispensed or infused into a patient. The inventors also envision that the invention may be used in desk-top or table-top settings, attached to or located near procedure tables and that it may be attached to any surface, plane, hook, loop, etc by way of a retention means, thereby allowing the apparatus to be used in a wide range of ambulatory field environments.

A preferred embodiment of the invention uses light emitting diodes (LEDs) as a light source, though other light sources such as electroluminescent lights might conceivably also be used. The LEDs can be powered by internally stored batteries, rechargeable or not, or by an external low-voltage power supply or by a combination of batteries and external power source or by other suitable methods.

FIG. 1A is a perspective view of the front and one side of the single intravenous drip components illumination device 10 according to the present invention, showing the two main components which are a light containing base portion 12 and a moveable back portion 14. FIG. 1B is a perspective view of one side and the rear of the single intravenous drip components illumination device 10 comprised of the base portion 12 and moveable back portion 14. In both FIGURES, a base illuminator assembly 16 on the base portion 12 incorporates a window 18 beneath which (i.e., inside the illuminator 16) is an array of LEDs (not shown). FIG. 1C shows an intravenous drip bag 20 hanging from the hook nib 22 at the top of the moveable back portion 14. The bag 20 is being lit by light rays 24 emanating from the base illuminator assembly 16.

FIGS. 1A, 1B and 1C also show the on/off switch 26, electrical input receptacle 28 and, in the partial backside view shown in FIG. 1B, the IV pole support brackets 30 with which the present invention can be attached to a vertical IV support pole (not shown). The presence of the power receptacle 28 is not meant to imply that external power is the only source of energy for the light source in the base illuminator assembly 16; the inventors conceive that batteries, rechargeable or not, can be incorporated within the base portion 12 and used with or without the benefit of a source of electrical energy that is external to the invention. FIG. 1B also shows a large hook ring 32 from which the single intravenous drip component illumination device 10 can be hung from a support structure (not shown). The hook ring 32 is attached to the back portion 14 by way of the integral structure 34 having a hole therethrough. And a spring release latch device 36, with a finger pull ring 38 secured thereto, serves to lock the moveable back portion 14 to the base portion 12 in a plurality of vertical positions, as described hereinbelow.

The darkened surface 13 on the base portion 12 provides a background that enhances the visibility of the IV drip components being lit by the illuminator assembly 16.

FIG. 2A is an orthogonal side view of the base portion 12 of the present single intravenous drip components illumination device, with the moveable back portion 14 removed and shown separately in orthogonal rear view in FIG. 2C and in orthogonal side view in FIG. 2D. FIG. 2E shows the fully assembled single intravenous drip component illumination device 10 in orthogonal side view. FIG. 2B shows the base illuminator assembly 16 from the direction of the arrow A in FIG. 2A. The base illuminator assembly 16 is comprised of a transparent window 18 beneath which are light sources such as light-emitting diodes (LEDs). Other portions of the base illuminator assembly are made of translucent to opaque material so as to prohibit lateral scattering of light from the LEDs or other light sources, so that the light shines primarily upward, toward and illuminates a suspended IV bag and the other IV drip components. The base illuminator assembly 16 of the preferred embodiment of the present invention contains four white LEDs 21 which are mounted upon a circuit board located in the portion of the base illuminator assembly opposite the window 18. Light from the LEDs 21 shines upward upon the intravenous drip bag 20 and the other IV drip components as shown in FIG. 1C.

Figure 3B:
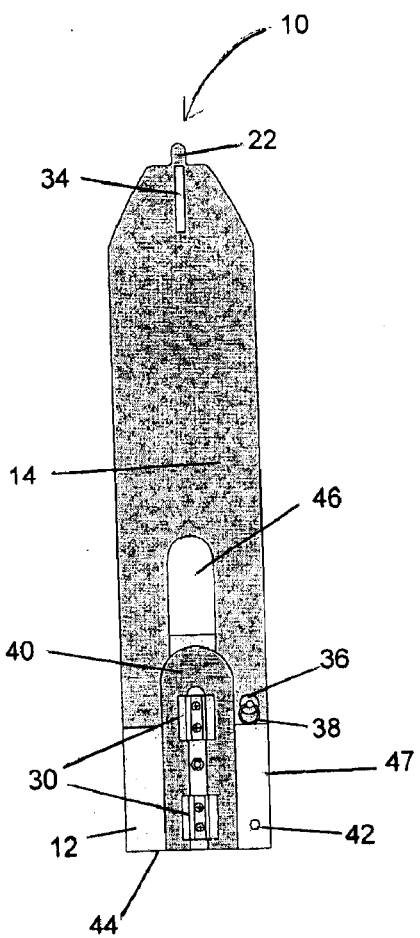
FIG. 3B is an orthogonal rear view of the moveable back portion shown in its raised position relative to the base portion.

An additional feature of the assembled single intravenous drip component illumination device 10 according to the present invention is shown in FIGS. 3A and 3B. In FIG. 3A, the moveable back portion 14 is shown in its lowest position relative to the bottom 44 of the base portion 12. In FIG. 3B, the moveable back portion 14 is shown in its elevated position relative to the base portion. The two or more different positions of the back portion of the invention 10 are intended to accommodate IV drip bags of varying sizes, or to accommodate other situations wherein the greater overall height of the invention might be useful. The spring-loaded plunger type latch or locking device 36 has a finger pull ring 38 with which the plunger can be withdrawn from the hole 42 in the base portion 12, as shown in FIG. 3B, thereby freeing the moveable backing plate 14 to be moved to and locked into two or more different positions. The spring-loaded plunger type locking device 36 engages a hole 42, shown in FIG. 3B, so as to lock the backing plate 14 firmly to the base portion 12 in the elevated position.

The flange plate 40 shown in FIGS. 3A and 3B is also shown in side view in FIG. 2A. Those skilled in the art will readily understand the way that the slot 46 in the moveable back plate 14 (as shown in FIGS. 2C and 3B) engages a corresponding sheet of material 48, shown in FIG. 2A to be disposed between the flange 40 and the back wall 47 of the base portion 12.

The inventors envision that two or more of the single intravenous drip components illumination devices 10 according to the present invention can be ganged together so as to hold multiple bags or bottles of IV solutions of different types, for use with multiple patients or with single patients or for other purposes. The inventors further envision that ganged single intravenous drip components illumination devices 10 can be distinguished from one another in dark settings by way of the use of color filters that can be laid over or otherwise attached to the respective windows 18 of the illuminator assemblies 16 of each unit 10 ganged together. Alternatively, the inventors envision that the illuminator assembly can use red, green and blue LEDs having individual controls so that individual primary colors can be "dialed in," thereby producing any desired identifying illuminating light color.

We claim:

1. An apparatus for supporting and illuminating intravenous drip components comprising:

a base portion comprising a visible light emitting device positioned to illuminate the drip components; and a back portion for vertically supporting the drip components, wherein said back portion is vertically connected to said base portion;

wherein said base portion is configured to support itself and said back portion in an upright, free-standing position.

2. The apparatus of claim 1 wherein said visible light emitting device comprises a plurality of light emitting diodes.

3. The apparatus of claim 2 wherein said visible light emitting device further comprises a plurality of movable light source lenses of various colors.

4. The apparatus of claim 1 wherein said base portion further comprises batteries as a power source for the visible light emitting device.

5. The apparatus of claim 1 further comprising an external low-voltage power supply as a power source for the visible light emitting device.

6. The apparatus of claim 1 wherein said back portion is slidably connected to said base portion.

7. The apparatus of claim 1 wherein said base portion further comprises brackets for securing the apparatus to a standard intravenous pole.

8. The apparatus of claim 1 wherein said back portion comprises a means for hanging the apparatus from a support structure.

9. The apparatus of claim 1 wherein said base portion further comprises brackets for securing a plurality of the apparatus together.

* * * * *